United States Patent
Yukon (10) Patent No.: US 8,318,010 B2
(45) Date of Patent: Nov. 27, 2012

(54) QUICK DISCONNECT LIQUID CHROMATOGRAPH COLUMNS

(76) Inventor: E. Daniel Yukon, Stoughton, MA (US)

(*) Notice: Subject to any disclaimer, the term of this patent is extended or adjusted under 35 U.S.C. 154(b) by 369 days.

(21) Appl. No.: 12/772,808

(22) Filed: May 3, 2010

(65) Prior Publication Data

US 2010/0206813 A1    Aug. 19, 2010

Related U.S. Application Data

(63) Continuation-in-part of application No. 12/364,324, filed on Feb. 2, 2009, now Pat. No. 7,901,574.

(51) Int. Cl.
B01D 15/08    (2006.01)

(52) U.S. Cl. .............. 210/198.2; 210/232; 210/656; 96/101; 285/33; 285/39; 285/388

(58) Field of Classification Search .......... 285/33, 285/39, 388; 210/656, 198.2, 232; 96/101, 96/106
See application file for complete search history.

(56) References Cited

U.S. PATENT DOCUMENTS

| | | | |
|---|---|---|---|
| 944,877 A | 12/1909 | Koschinski |
| 1,726,683 A | 9/1929 | Schramm |
| 1,977,179 A | 10/1934 | Fisch |
| 2,225,654 A | 12/1940 | Olson |
| 3,487,938 A | 1/1970 | Patterson |
| 3,488,073 A | 1/1970 | Wold |
| 4,313,828 A | 2/1982 | Brownlee |
| 4,343,496 A | 8/1982 | Petranto |
| 4,451,364 A | 5/1984 | Higgins et al. |
| 4,451,365 A | 5/1984 | Sattler et al. |
| 4,586,733 A | 5/1986 | Anderson, Jr. |
| 4,737,284 A | 4/1988 | Hauke et al. |
| 4,806,238 A | 2/1989 | Sattler et al. |
| 4,865,728 A | 9/1989 | Larsson |
| 4,876,005 A | 10/1989 | America |
| 4,968,421 A | 11/1990 | Spacek et al. |
| 5,167,810 A | 12/1992 | Vassarotti et al. |
| 5,194,225 A | 3/1993 | Muller et al. |
| 5,299,842 A | 4/1994 | Marks et al. |

(Continued)

FOREIGN PATENT DOCUMENTS

EP    0 476 995    3/1992

(Continued)

Primary Examiner — Ernest G Therkorn
(74) Attorney, Agent, or Firm — Sampson & Associates, P.C.

(57) ABSTRACT

A chromatography column and method for use in a liquid chromatography process includes a telescoping chromatography and piston tubes, with the piston tube having a porous layer partially obstructing flow therethrough. A chromatography clamp is selectively movable between open and closed positions, and configured to extend substantially 360 degrees about the periphery of the chromatography tube when closed. The chromatography clamp is configured to releasably maintain the chromatography tube and piston tube in fluid communication with one another. In particular embodiments, the chromatography clamp includes a ledge extending at an oblique angle relative to the transverse direction, which is configured to cam the clamp towards the closed position upon application of greater than atmospheric pressure within the chromatography column.

23 Claims, 9 Drawing Sheets

U.S. PATENT DOCUMENTS

| | | |
|---|---|---|
| 5,366,621 A | 11/1994 | Bidell et al. |
| 5,378,361 A | 1/1995 | Baeckstrum |
| 5,601,708 A | 2/1997 | Leavesley |
| 6,090,190 A | 7/2000 | Enhsen et al. |
| 6,171,486 B1 | 1/2001 | Green et al. |
| 6,932,904 B2 | 8/2005 | Laub et al. |
| 7,364,655 B2 | 4/2008 | Demarco |
| 7,901,574 B2 * | 3/2011 | Yukon .................. 210/198.2 |
| 2007/0090035 A1 | 4/2007 | Rahn et al. |
| 2007/0170110 A1 | 7/2007 | Onoue et al. |
| 2008/0230454 A1 | 9/2008 | Nibler et al. |

FOREIGN PATENT DOCUMENTS

| | | |
|---|---|---|
| EP | 1 306 668 | 10/2002 |
| EP | 1306668 | 5/2003 |
| JP | 2007-071730 | 3/2007 |
| JP | 2007-71730 | 3/2007 |
| JP | 200771730 | 3/2007 |

* cited by examiner

QUICK DISCONNECT LIQUID CHROMATOGRAPH COLUMNS

RELATED APPLICATIONS

This application claims priority, and is a Continuation-In-Part of U.S. patent application Ser. No. 12/364,324, entitled Quick Disconnect Liquid Chromatograph Columns, filed Feb. 2, 2009, now U.S. Pat. No. 7,901,574 the contents of which are incorporated herein by reference in their entirety for all purposes.

TECHNICAL FIELD

This invention relates to liquid chromatography and more particularly to liquid chromatography columns.

BACKGROUND INFORMATION

Chromatography (from Greek χρώμα:chroma, color and γραφειν:graphein to write) is the collective term for a family of laboratory techniques for the separation of mixtures. It involves passing a mixture dissolved in a "mobile phase" through a "stationary phase", which separates the analyte to be measured from other molecules in the mixture and allows it to be isolated.

Liquid chromatography is one subset of chromatography processes used for chemical separation. A liquid eluent/mobile phase is passed through an adsorbent/stationary phase. This stationary phase, in many systems, is contained in a chromatography column.

In 1978 W. C. Still introduced an improved form of column chromatography called flash column chromatography where the eluent or mobile phase is pushed through the column, containing the stationary phase, under a positive pressure. This pressure can be substantial.

Before being used, a chromatography tube must typically first be packed with the stationary phase such that it is evenly distributed to achieve the best possible separation in the chromatography process. This may be accomplished in various ways but it is desirable for the result to be a fully packed chromatography tube with evenly distributed stationary phase particles which typically vary in size within a given manufactured range.

Interchangeable chromatography columns which can be attached in line with a chromatography process come in a variety of different configurations. It is important that these columns can be efficiently connected and disconnected to the chromatography system. One of the practical problems with these existing configurations is that disconnecting them in liquid chromatography systems can be physically difficult for technicians due to residual pressure in the system. Physical acts such as pushing against pressure and turning, or unscrewing a pressure loaded connection may place a technician in a position where they undergo harmful repetitive motion in their work or have to rely on third parties to perform these tasks.

A need therefore exists for improved liquid chromatograph columns that address these drawbacks.

SUMMARY

In accordance with one aspect of the invention, a chromatography column is provided for use in a liquid chromatography process. The column includes a chromatography tube and a piston tube having an outer diameter smaller than the inner diameter of the chromatography tube. The piston tube has at least one porous layer partially obstructing flow therethrough. At least one chromatography clamp is selectively movable between open and closed positions, and configured to extend substantially 360 degrees about the periphery of the chromatography tube when closed, with no single component of said chromatography clamp extending substantially 360 degrees about said chromatography tube. The chromatography clamp is configured to releasably maintain the chromatography tube and piston tube in fluid communication with one another.

In a variation of the foregoing aspect, the chromatography clamp includes a ledge extending at an oblique angle relative to the transverse direction, which is configured to cam the clamp towards the closed position upon application of greater than atmospheric pressure within the column.

Another aspect includes a method for performing liquid chromatography. The method includes providing a chromatography tube having a predetermined inner diameter, and providing a piston tube having an outer diameter smaller than the inner diameter of the chromatography tube, the piston tube having at least one porous layer partially obstructing flow through the piston tube. At least one chromatography clamp is provided, the clamp configured for being selectively movable between open and closed positions, and configured to extend substantially 360 degrees about the periphery of the chromatography tube when closed, with no single component of the chromatography clamp extending substantially 360 degrees about the chromatography tube. The clamp is closed about ends of both the chromatography tube and the piston tube, so that the tubes are releasably maintained in fluid communication with one another. Fluid is supplied to the piston tube.

In a variation of the foregoing method, the chromatography clamp has a ledge extending at an oblique angle to the transverse direction and configured to cam the clamp towards the closed position upon application of greater than atmospheric pressure within the chromatography tube, and fluid is supplied to the chromatography tube so that the pressure therein exceeds atmospheric pressure and the clamp is cammed towards the closed position.

In a still further aspect of the invention a chromatography column is provided for use in a liquid chromatography process to convey eluent through the column and through an adsorbent disposed within the column. The column includes a chromatography tube and a piston tube having an outer diameter smaller than an inner diameter of the chromatography tube. The piston tube has at least one porous layer partially obstructing flow through the piston tube. A collar is configured to capture the piston tube, and has a collar ledge. At least one chromatography clamp is selectively movable between open and closed positions, and configured to extend substantially 360 degrees about the periphery of said chromatography tube when closed, with no single component of said chromatography clamp extending substantially 360 degrees about the chromatography tube. The chromatography clamp has a clamp ledge extending at an oblique angle relative to the transverse direction, the clamp ledge configured to engage the collar ledge to cam the clamp towards the closed position upon application of greater than atmospheric pressure within the column. The chromatography clamp is configured to releasably maintain the chromatography tube and the piston tube in fluid communication with one another.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Applicant has devised a new chromatography column that allows for the convenient exchange of chromatography tubes in a chromatography system. The applicant has configured a column with a quick release chromatography clamp that allows the technician to easily connect and disconnect the column with a minimal application of force. This allows for easier and faster transfer of chromatography tubes to reduce the burden on technicians and improve system efficiency relative to prior approaches.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

An embodiment of the subject invention includes a chromatography tube. At each open end of the chromatography tube a chromatography clamp, threaded on its interior surface, is used to capture and hold a piston tube, threaded on its exterior surface, in fluid communication with the aforementioned chromatography tube. The clamp captures a flange on the end of the chromatography tube and the threads of the piston tube, thereby holding the tubes in alignment. The chromatography tube is configured to receive a particulate solid therein. This solid is restrained from passing through the tube by a porous obstruction, such as a screen, which may be located across one end of the piston tube. The piston tube is restrained from rotating relative to the chromatography tube, by a medium such as a flexible o-ring that fits between the inner piston tube and outer chromatography tube. The closed chromatography clamp is free to rotate around the piston tube and chromatography tube. In doing so the clamp forces the piston tube to move axially relative to the chromatography tube, such as to compact the particulate solid therein. Fluid may then be pumped in through one piston tube into the chromatography tube where it interacts with the particulate. Separation occurs, in a conventional manner recognizable to one skilled in the art. The fluid then flows out the opposite piston tube where it is collected.

Once the process has been completed the pumping of the fluid is stopped and the quick release clasp on each clamp may be easily unfastened. The chromatography tube, with the spent particulate solid stationary phase, may then be removed and quickly and easily replaced in order to begin a new process.

Figure 2:
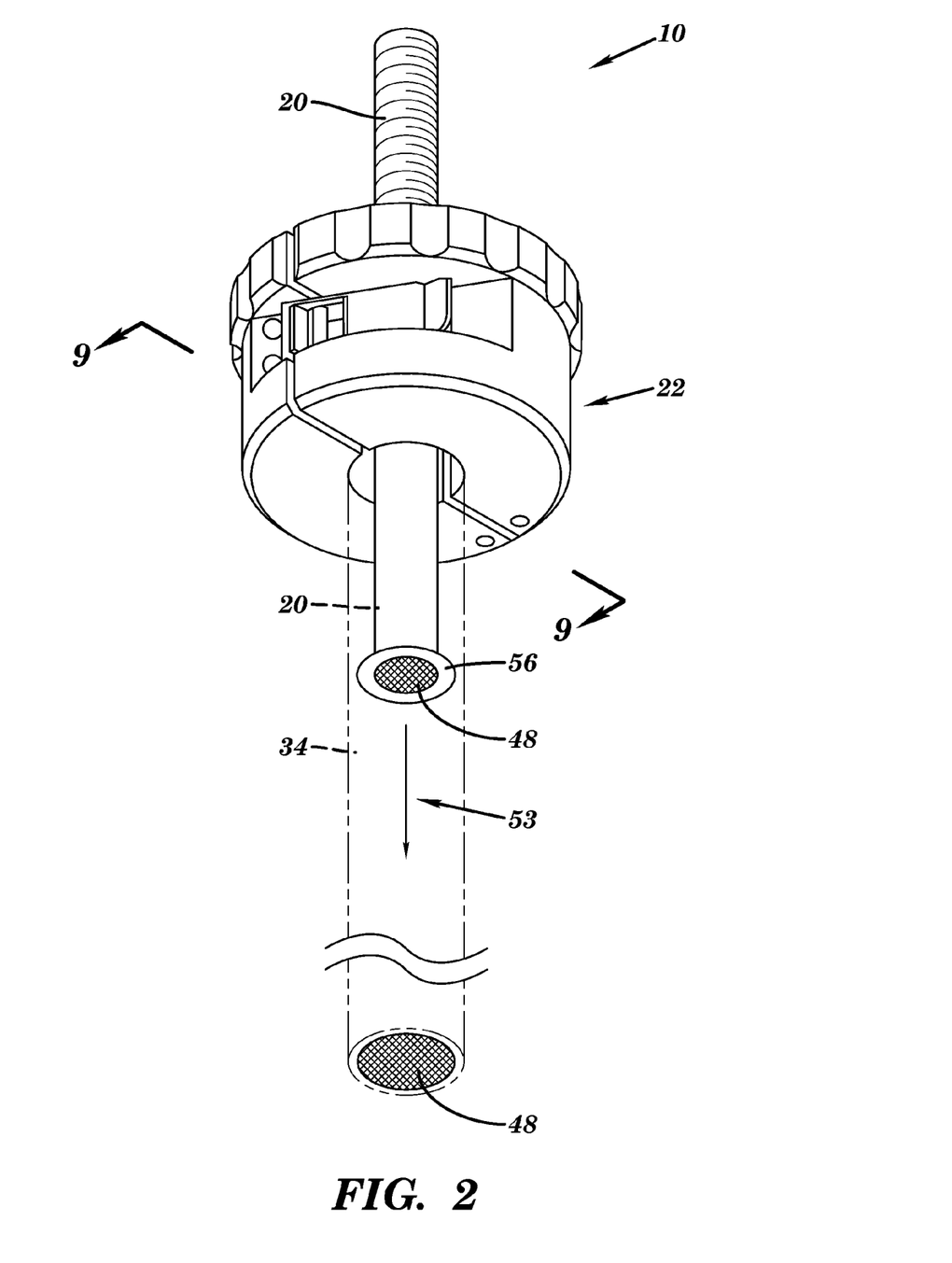
FIG. 2 is a perspective view, with portions broken away, of an embodiment of the subject invention usable in FIG. 1.

In some embodiments, the clamp may be essentially take the form of a single piece including two halves secured to one another by a movable connecter such as a hinge. This means relatively few components to keep track of when installing the column. Since the clamping force is approached substantially from the sides (i.e., using a lateral application of force), rather than from the ends (using an axial application of force), manipulating the fastener to open or close the clamp has the additional benefit of requiring the application of substantially less force than conventional approaches that involve twisting or turning a threaded connector.

Where used in this disclosure, the term "axial" when used in connection with an element described herein, refers to a direction parallel to the flow path and/or downstream flow of the process solution therethrough (e.g., shown at 53, FIG. 2). The term "axial plane" refers to a plane that would include a vector in the axial direction. Similarly, the term "transverse" refers to a direction substantially orthogonal to the axial direction. The term upstream is used to describe the direction from which the process fluid is introduced into the column, likewise downstream is used to describe the direction in which the process fluid would exit the column.

Figure 1:
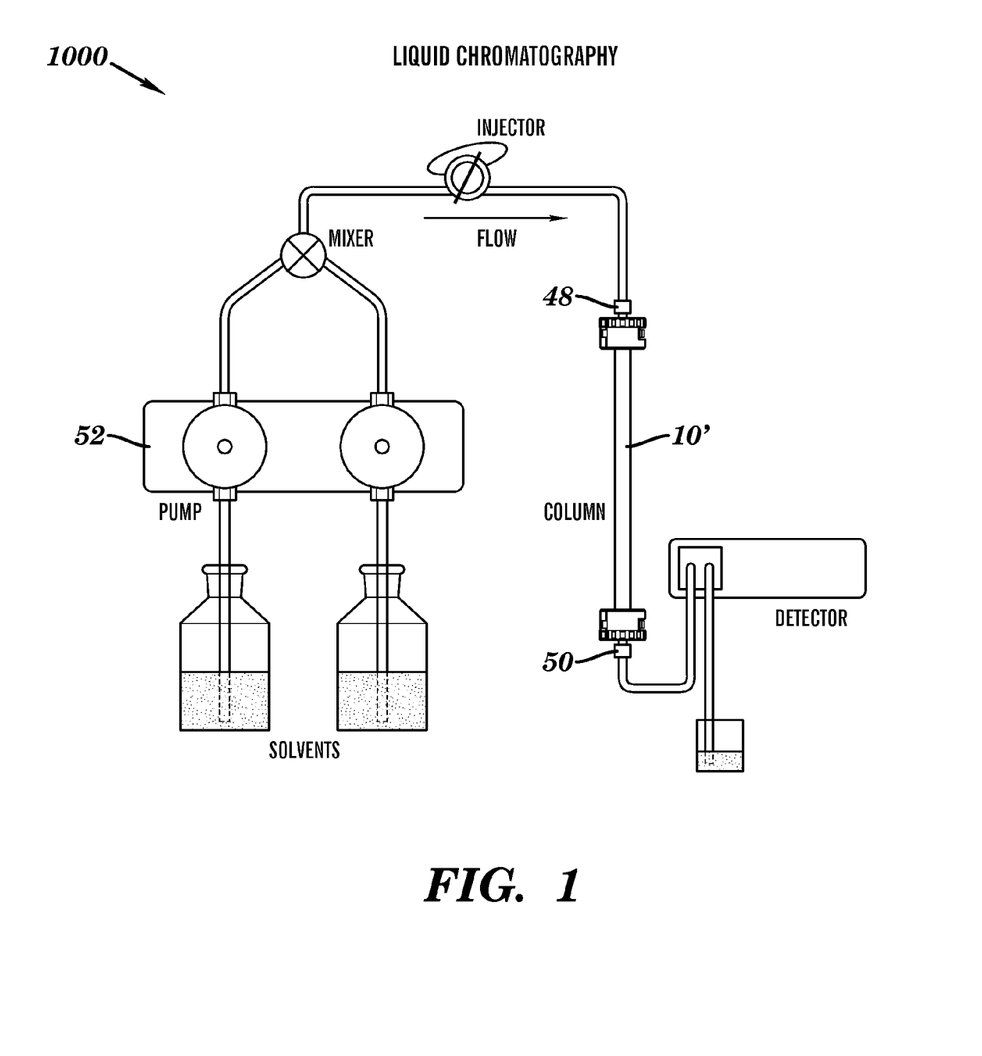
FIG. 1 is a schematic view of an embodiment of the present invention incorporated into a chromatography process.

Turning now to the figures, embodiments of the present invention will be discussed in detail. Referring to FIG. 1, an embodiment of the chromatography column (10') is shown incorporated into a typical chromatography process (1000). A piston tube (20, FIG. 2) may be connected via a conventional threaded pressure fitting to upstream and downstream connections (48, 50). The piston tubes (20) are connected via a clamp (22, FIG. 2) to opposite ends of a chromatography tube (34, FIG. 2) of column 10'. A pump (52) is configured to force fluid under pressure through the upstream connection 48, to the chromatography column (10') which contains a particulate stationary phase. The interaction of the process fluid (eluent) with the stationary phase (adsorbent) separates the analyte (the material to be separated) from the fluid solution.

Having described a representative chromatography process within which various embodiments of the invention may be employed, these embodiments will now be described in detail. Referring to FIG. 2, one embodiment of a chromatography column for use in a liquid chromatography process is shown at (10). This column (10) includes a chromatography tube (34) shown in phantom for clarity, a chromatography clamp (22), a collar or nut block (26, FIG. 3), and a piston tube (20). The piston tube (20) has a smaller outer diameter than the inner diameter of the chromatography tube (34). The nut block (26, FIG. 3) is threadably engaged with the piston tube (20). When the chromatography clamp (22), which in the embodiment shown separates along its axial plane (54, FIG. 3), is closed and fastened to couple and seal the piston tube (20) to an end of the chromatography tube (34), the nut block (26, FIG. 3) is held in place and is substantially prevented from rotating relative to the chromatography clamp (22). A porous obstruction, such as a screen (48), may be located at the end of the piston tube (20) most interior to the chromatography tube, in order to partially obstruct flow therethrough, e.g., to substantially prevent a particulate stationary phase (inserted by a user as discussed in greater detail hereinbelow) from passing into the piston tube (20).

The piston tube (20) is substantially prevented from rotating relative to the chromatography tube (34) by the use of an o-ring (56) disposed in a substantially fluid-tight fit between tubes (34) and (20). As shown, it may be desirable to locate the o-ring (56) close to the (interior) end of the piston tube (20) having the porous obstruction, to help minimize any movement of the stationary phase particles into the clearance between the piston tube (20) and the chromatography tube (34). The piston tube (20) may also be provided with an annular groove (FIG. 9) sized and shaped to receive and capture the o-ring (56) at this desired location. The groove may be provided in any convenient manner, such as by machining, molding, etching, etc. The clamp (22) is configured to rotate relative to both the chromatography tube (34) and piston tube (20) to exert an axial force, via the threaded engagement with nut block (26, FIG. 3), tending to move the piston tube (20) axially relative to the chromatography tube (34).

Is should be noted that the end of the chromatography tube opposite the clamp may be coupled to the chromatography process in substantially any manner known to those skilled in the art. For example, a second clamp 22, including its own piston tube and porous obstruction may be used, as with column 10' of FIG. 3, discussed below. Alternatively, a nozzle, filter or other type of obstruction may be provided to prevent the stationary phase from passing out of the chromatography tube (34) while still allowing the process fluid to flow through the tube (34). For example, one such optional approach would be to provide column (10) with a second porous obstruction (48) disposed substantially permanently near the open end of the chromatography tube (34) opposite the clamp (22) as shown in phantom. This may eliminate the need for use of a second clamp (22) at that open end.

Figure 3:
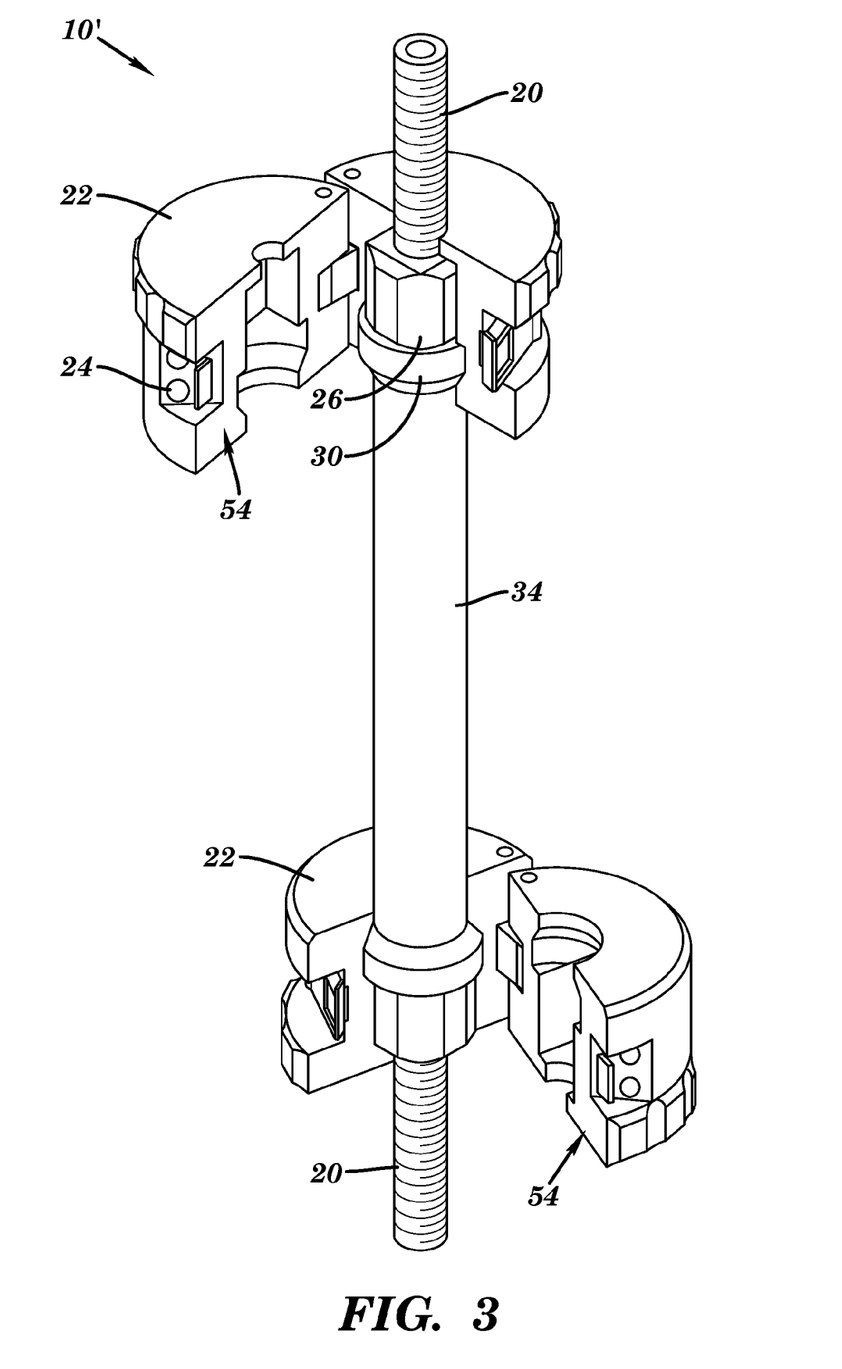
FIG. 3 is a perspective view of an alternate embodiment of the subject invention.

Referring to FIG. 3, in another embodiment, a chromatography column (10') is substantially similar to column 10, while also including a second chromatography clamp (22), and a second piston tube (20). The two chromatography clamps (22), which separate along their axial planes (54), are configured to be closed and fastened to couple and seal a piston tube (20) to each end of chromatography tube (34), to maintain the tubes in fluid communication with one another. The piston tubes (20) may each have a porous obstruction (48) (FIG. 1), such as a screen, located at the ends of the piston tubes (20) most interior to the chromatography tube (34). The ends of the piston tubes (20) farthest away from the chromatography tube (34) may be threaded or otherwise fitted with a relatively high pressure connection for attaching the column 10' in line with a chromatography process such as process 1000 of FIG. 1. The quick release clasps (24) may be easily fastened and unfastened allowing the clamps (22) to be respectively closed and opened to easily connect and disconnect a column 10' from a process.

Figure 4:
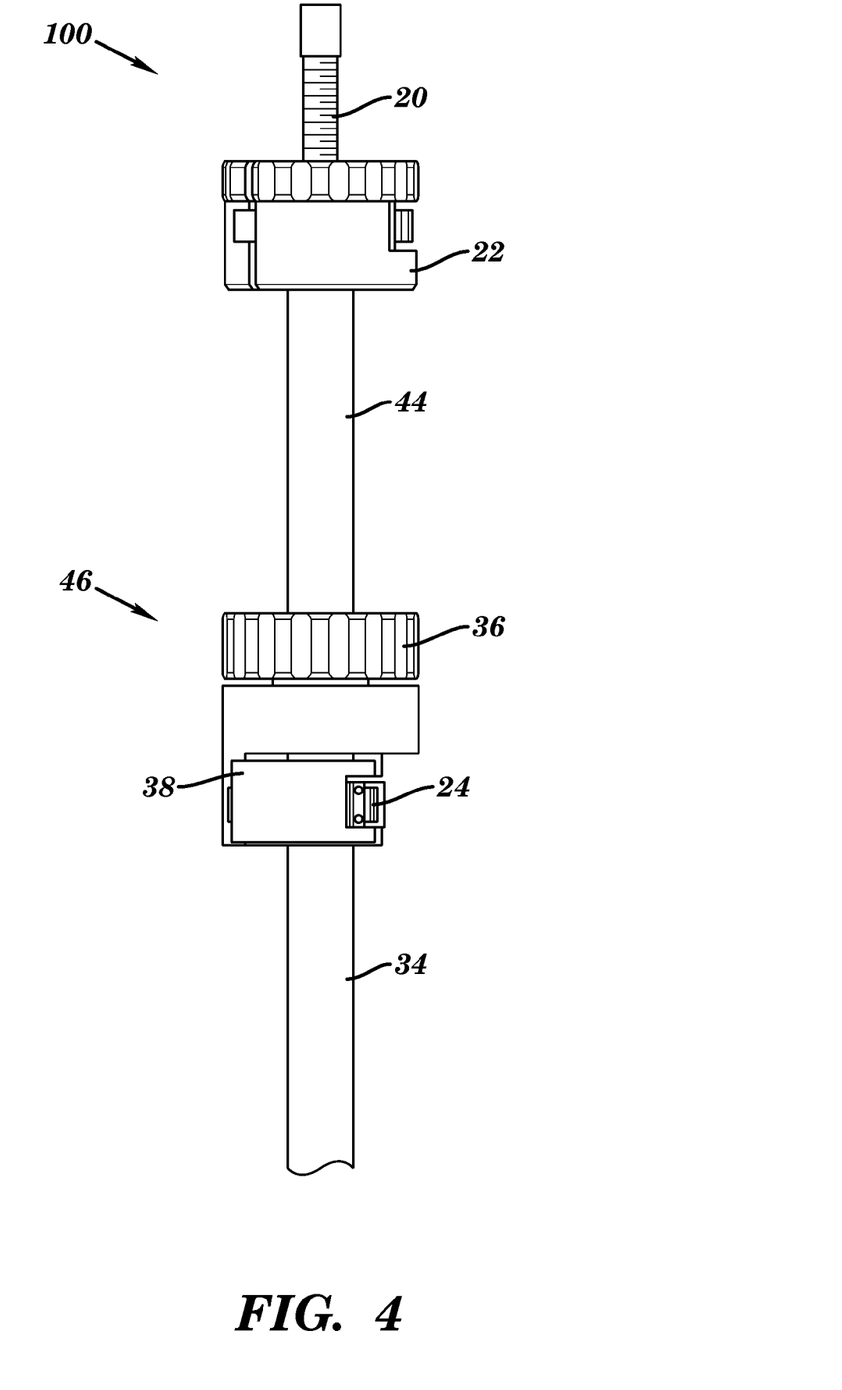
FIG. 4 is a side view of an alternate embodiment of the subject invention.

Referring to FIG. 4, another embodiment is shown as filler assembly (100), which may be used to fill or "pack" the chromatography tubes (34) of FIGS. 1&2 with a slurry including a mixture of stationary phase particulate and a fluid. This "packing" process is described in greater detail below. The filler assembly (100), in the embodiment shown, includes a filler tube (44), a column coupling clamp (46) and a clamp (22). As shown, tube (34) of the embodiments of either FIG. 2 or 3, may be removed from its clamp (22), and communicably coupled to filler tube (44) using column coupling clamp (46).

Figure 5:
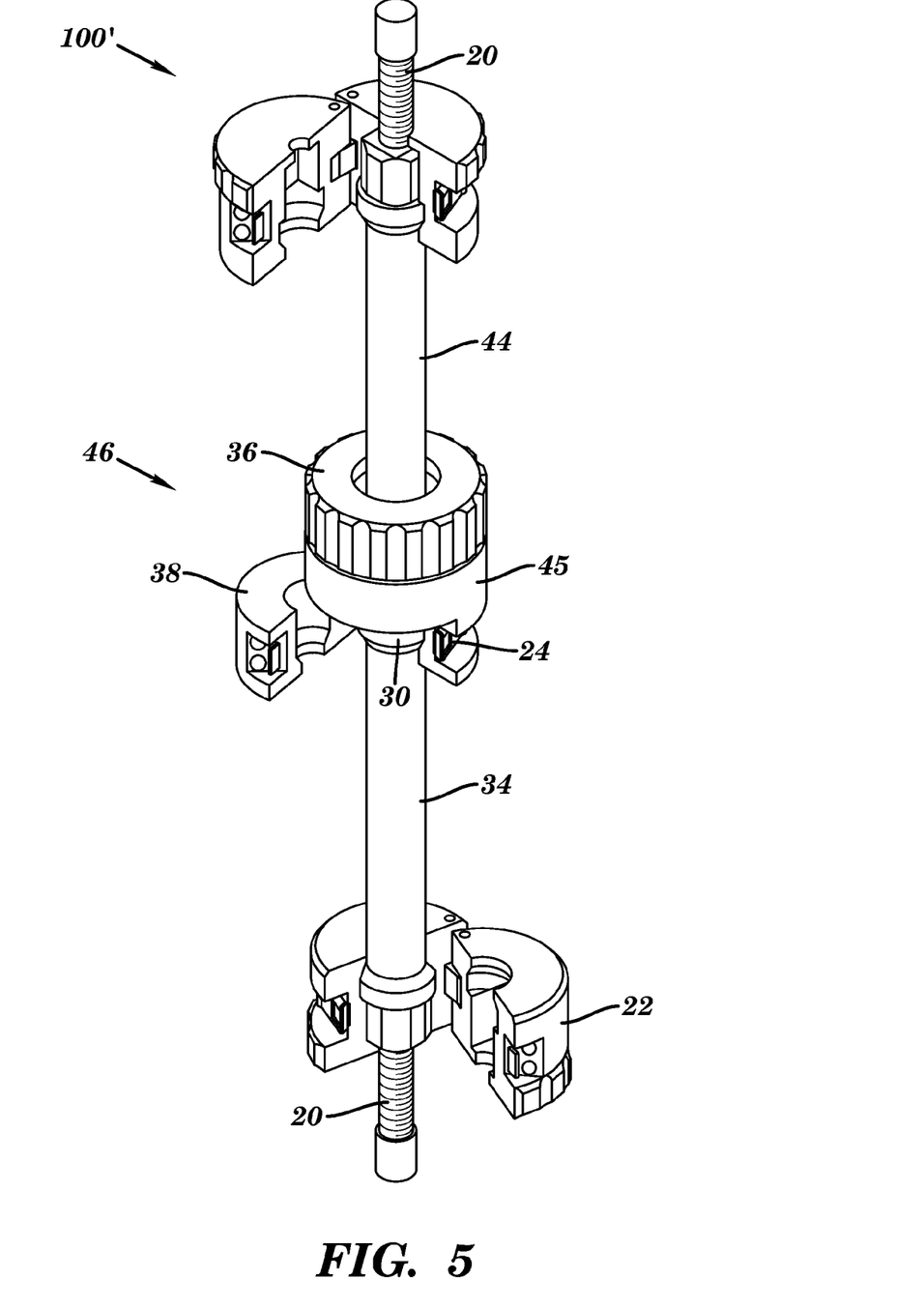
FIG. 5 is a perspective view of another alternate embodiment of the subject invention.

The coupling clamp (46), as best shown in FIG. 5, operates to capture the chromatography tube (34) by utilizing an axial clamp seal (38) which closes around the flange (30) of chromatography tube (34) and is held closed by a fastener such as a clasp (24). The filler tube (44) may be captured, via a flanged end thereof, by a screw cap (36) threadably engaged with body (45) of coupling clamp (46). In this regard, the screw cap (36) may be substantially annular, having an inner diameter larger than the diameter of filler tube (44) as shown, but smaller than the outer diameter of the flanged end of the filler tube (44). A person skilled in the art will recognize that the use of a flexible broken washer, elastomeric o-ring or other comparable device may be used to improve the seal at the connection point(s) between the filler tube (44) and the screw cap (36)/body (45). When the screw cap (36) is threadably engaged with body (45) of coupling clamp (46), filler tube (44) is captured and held in fluid communication with the chromatography tube (34). A clamp (22), such as shown and described with respect to FIGS. 2 and 3, may be used to engage a flanged end of the filler tube (44) opposite the column coupling clamp (46) and hold it in fluid communication with a piston tube (20). Similarly, the end of tube (34) opposite clamp (46) may be provided with an obstruction 48, such as shown and described hereinabove with respect to FIG. 2.

Referring to FIG. 5, in an alternate embodiment, a tube assembly (100') is substantially similar to the tube assembly 100 with a second clamp (22) disposed at the end of the chromatography tube (34) opposite the end captured by the column coupling clamp (46). This clamp (22) thus maintains the chromatography tube (34) in fluid communication with a second piston tube (20) as shown.

The various components shown and described herein may be fabricated from substantially any material having the necessary physical properties required for conventional chromatography operations. Without restricting the possible materials that may be employed, the applicant submits the following examples of exemplary materials that may be used to manufacture various components: Borosilicate glass for the chromatography and filler tubes (34,44); Teflon® fluorine-containing polymer (E.I. Du Pont De Nemours and Company, Wilmington Del.), Polypropylene or Peek for the piston tube (20); Polyethylene, Stainless Steel, Porous glass or Titanium for the porous obstruction (48); Delrin® synthetic resin (DuPont) for the clamp (22) and coupling clamp (46); Delrin® or Teflon® for the nut block, and Stainless steel for the clasp (24).

Note that the embodiments above are meant to illustrate various possible configurations of the present invention and the applicant does not restrict the application to these particular embodiments. As shown and described with respect to FIG. 2, one possible modification to any of the aforementioned embodiments and others would be to substantially permanently (e.g., immovably) dispose a porous obstruction (48) at one end of the chromatography tube (34). Such a modification may eliminate the need for a clamp (22) at that end of the tube (34), to reduce the number of clamps (22) needed to assemble the column.

Figure 7:
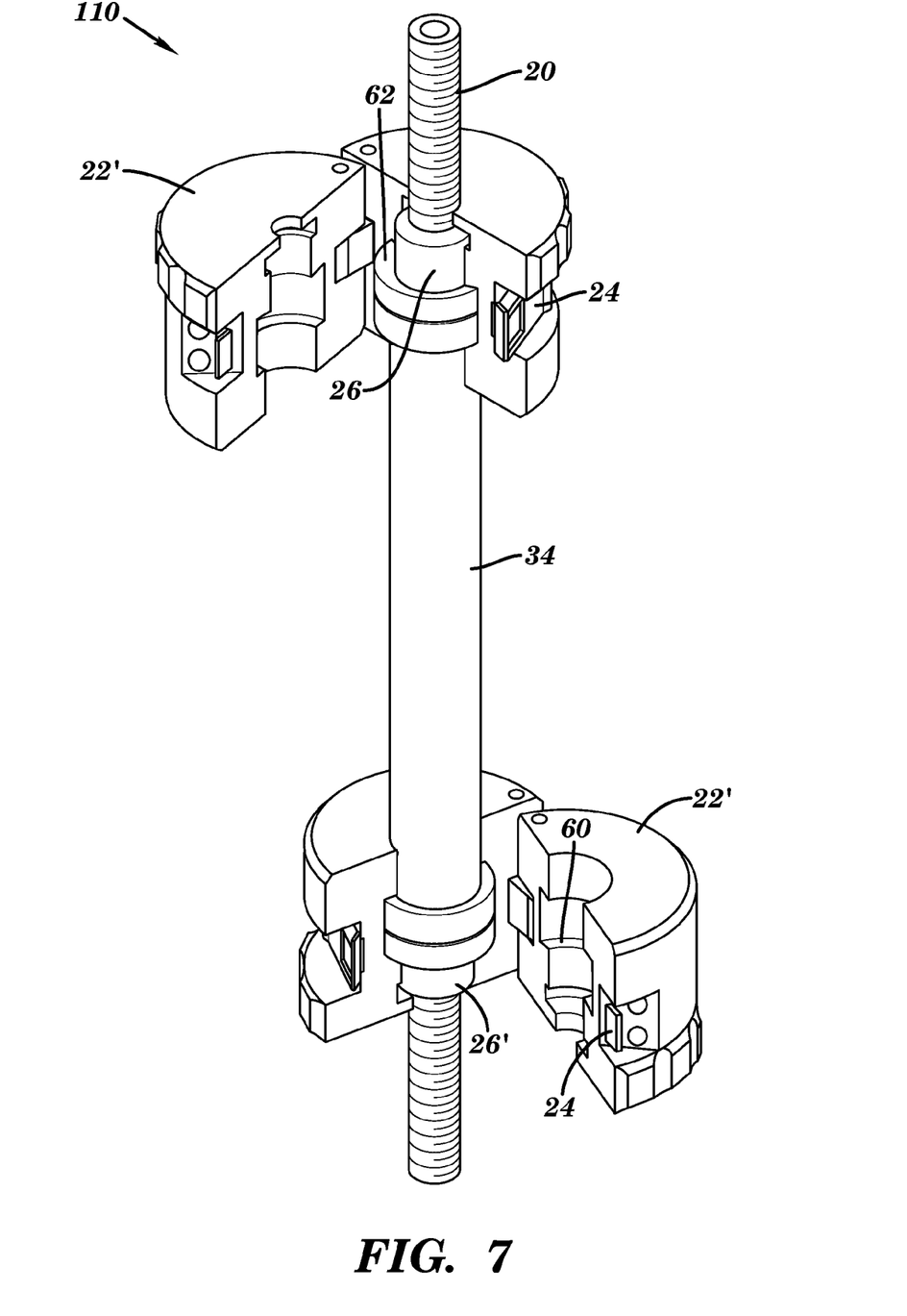
FIG. 7 is a perspective view showing a variation of the embodiment of FIG. 3.
Figure 8:
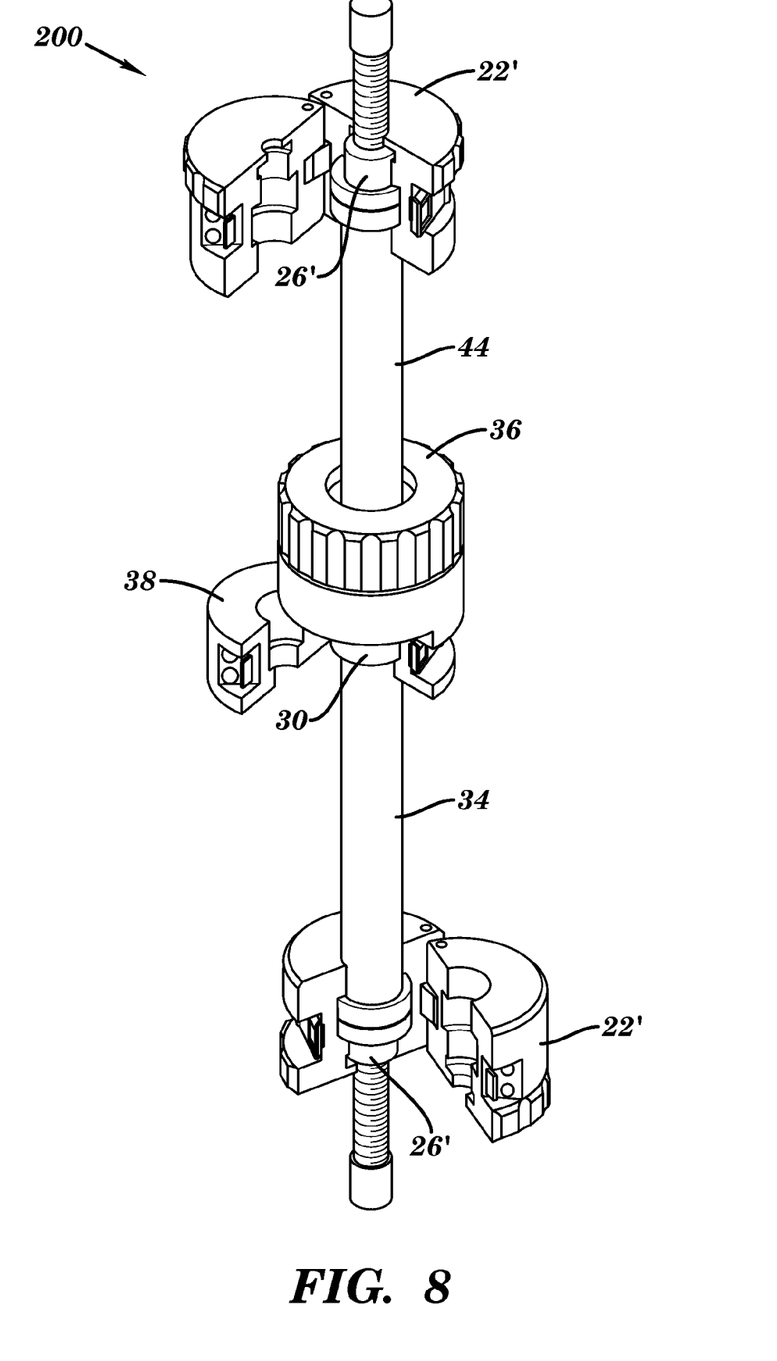
FIG. 8 is a perspective view showing a variation of the embodiment of FIG. 5.
Figure 9:
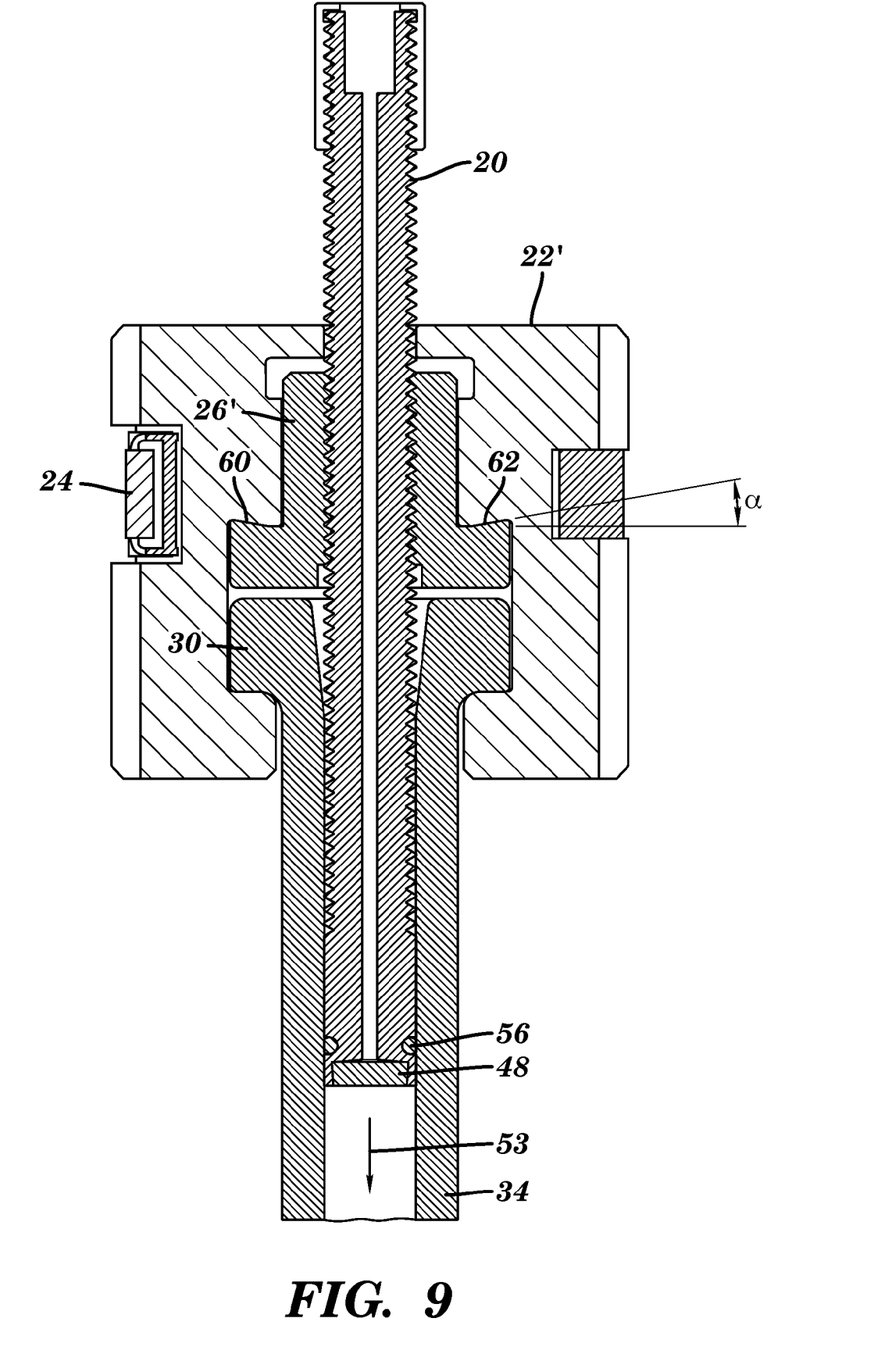
FIG. 9 is a cross-sectional view taken along 9-9 of FIG. 2, showing the variation of FIGS. 7-8.

Turning now to FIGS. 7-9, various additional embodiments of the subject invention may include any of the above-described chromatography columns and/or filler assemblies, modified to include a pressure-sealing chromatography clamp (22') and collar (26'). Examples of these additional embodiments are shown as chromatography column (110) in FIG. 7 and filler assembly (200) of FIG. 8. It should be recognized that clamp (22') (and collar 26') may be applied to substantially any of the embodiments shown and described herein, without departing from the present invention.

As shown in FIG. 7, a chromatography column (110) is substantially similar to column (10') of FIG. 3, but for the use of pressure-sealing chromatography clamps (22') and collars (26') disposed at each end of the tube (34). Column (110), including clamps (22'), operates in substantially the same manner as described with respect to column (10'). As with clamps (22) of column (10'), the clamps (22') are configured to be alternately opened and closed by a user operating the quick release clasps (24). However, the pressure-sealing clamps (22') are configured so that pressure within the chromatography system, including column (110), tends to bias the clamps (22') towards their closed positions. This pressure-biasing thus tends to relieve stress from clasps (24) during chromatography operations, while also helping to prevent the clamps (22') from being inadvertently or carelessly opened before depressurizing the system.

Referring now to FIG. 8, filler assembly (200) is substantially similar to filler assembly (100') of FIG. 5, but for the use of pressure-sealing chromatography clamps (22') and collars (26'), instead of clamps and collars (22), (26). A user may operate assembly (200), including clamps (22'), in substantially the same manner as assembly (100'), with the clamps (22') configured to alternately open and close using the quick release clasps (24). However, as mentioned above, the pressure-sealing clamps (22') are configured so that pressure within the chromatography system (e.g., greater than ambient atmospheric pressure) tends to bias the clamps (22') into their closed positions.

Turning now to FIG. 9, pressure-sealing clamp (22') and collar (26') will be described in greater detail. As shown, clamp (22') is disposed about flange (30) at one end of a chromatography tube (34). Clamp (22') is configured to engage a collar or nut block (26'), which is threadably engaged with piston tube (20). This configuration thus maintains piston tube (20) in fluid communication with chromatography tube (34) substantially as described hereinabove with respect to clamp (22) and collar (26).

In this regard, the chromatography clamp (22') may be closed, e.g., by fastening quick release clasp (24), to communicably couple and seal the piston tube (20) to an end of the chromatography tube (34). When so positioned, the nut block (26') is held in place and is substantially prevented from rotating relative to the chromatography clamp (22'). The clamp (22') (along with nut block 26') may then be rotated relative to both the chromatography tube (34) and piston tube (20), to move the tube (20) axially within tube (34), by virtue of the threaded engagement of tube (20) with nut block/collar (26').

As also shown, clamp (22') is provided with a ledge (60) configured for being mated in surface-to-surface engagement with a similarly sized and shaped ledge (62) of nut block/collar (26'). Ledges (60), (62), each extend at an oblique angle alpha ($\alpha$) relative to the transverse dimension. Moreover, as also shown, angle alpha extends obliquely away from flange (30) to which the clamp (22') and collar (26') are fastened.

When so configured, the ledges (60), (62) effectively form cam surfaces that tend to cam the halves of clamp (22') radially inward towards the clamp's closed or "fastened" position as shown. Thus, when pressure builds within tube (34), e.g., during the chromatography process, the pressure tends to push the piston tube(s) 20 axially away from the end of the chromatography tube (34). This axial pressure tends to push the ledge (62) of collar (26') into engagement with the corresponding ledge (60) of clamp (22'), to provide camming action.

Substantially any angle alpha may be used, provided it is large enough to generate the described camming action. It should be recognized, however, that if the angle alpha is too large, then it may be difficult to open and close the clamp (22'), e.g., due to interference between the ledges (60), (62). On the other hand, if the angle alpha is too small, i.e., approaching zero degrees relative to the transverse direction, then the camming action may be insufficient to keep the clamp closed in the event relatively high internal pressures are used (while the latch is open). In some embodiments, angle alpha is approximately 15 degrees or less. In particular embodiments, an angle alpha in the range of about 3 to 10 degrees may be used. Moreover, in some applications, an angle alpha in the rang of 4 to 7 degrees may be used. In addition, although ledges (60) and (62) may be substantially continuously to form a disc or annulus extending about axis (53), such as shown in FIG. 7, it should be recognized that the ledges may be discontinuous, without departing from the scope of the present invention.

Although the cam surfaces have been shown and described as being formed by mating ledge surfaces (60), (62), it should be recognized that substantially any of the mating surfaces shown and described may be configured as cam surfaces, without departing from the scope of the present invention. For example, the substantially radially extending, mating surfaces of flange (30) and clamp (22') may be angled to provide the desired camming action.

Figure 6:
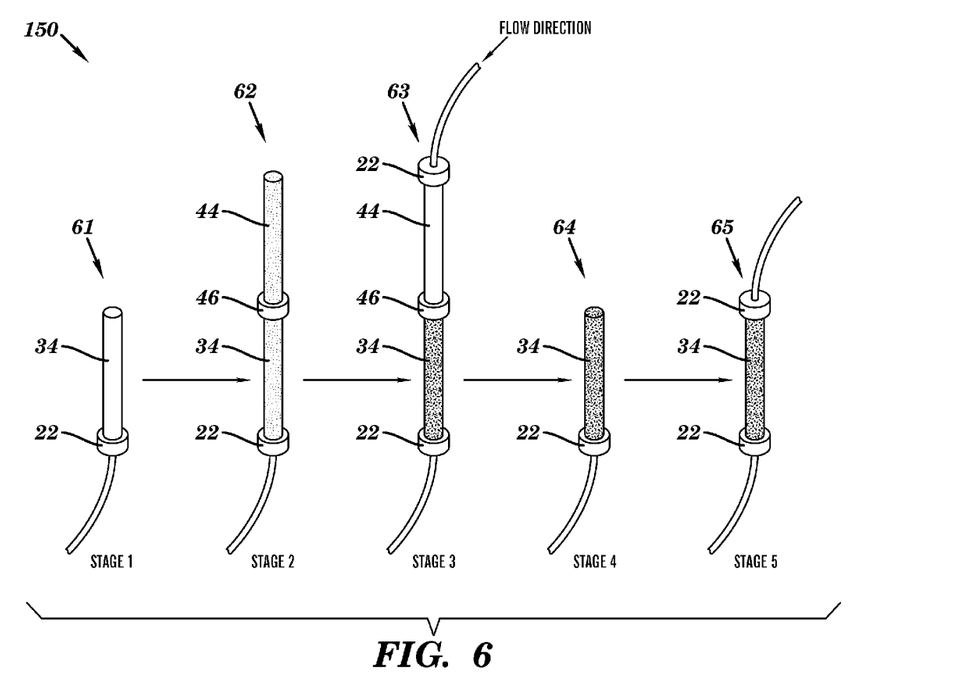
FIG. 6 is a flowchart showing a method of packing a chromatography column using an embodiment of the subject invention.

Referring to FIG. 6, a method (150) of packing a chromatography column with stationary phase material using a filler assembly, is shown and described. For convenience, this method (150) is shown and described using a column (10') and filler assembly (100'), although it should be recognized that this method 150 may be similarly applied to all of the embodiments shown and described herein, including columns (10), (110) and filler assemblies (100), (200). As mentioned hereinabove, prior to using a new or empty column (10'), the column is typically packed with stationary phase particles. Such stationary phase particles are well known to those skilled in the art, the most common being silica. A commercial example of a column-packing material used in newer systems includes GE Healthcare (Pharmacia) Superdex 75 (GE Healthcare, Piscataway N.J.). The stationary phase is typically purchased from a manufacturer in a range of particle sizes (e.g. a 10 micron media has a particle distribution of approximately 7-12 microns).

In a first stage (61) a single chromatography tube (34) is connected by a clamp (22) to the downstream portion of a chromatography system 1000 (FIG. 1). In the second stage, at (62), chromatography tube (34) is coupled to a filler tube (44) using a coupling clamp (46). Tube (34) is filled with a slurry including a chromatography process fluid (mobile phase) mixed with a solid particle stationary phase. For proper separation to occur in a chromatography process, it has been found that the particles are desirably packed with substantially even size distribution. One approach that may be used to help achieve such a distribution is slurry/flow packing. This typically includes mixing roughly equal parts of mobile phase and stationary phase outside the column in a suitable container (e.g., beaker). The mix is typically 1:1 ratio, in essence doubling the volume of the finished stationary phase volume. The column extension provided by filler tube (44) is configured to provide sufficient additional volume to enable the combination of tubes (34) and (44) to contain this mixture. The porous obstruction (48) (see, e.g., FIG. 2) at the downstream end of tube (34) helps to prevent the particulate stationary phase from exiting the chromatography tube (34) in the downstream direction.

In the third stage (63), a clamp (22) is closed around the open end of the filler tube (44) coupling the filler tube to a piston tube (20) and holding the column in fluid communication with the upstream portion of the chromatography system 1000 (FIG. 1). Fluid is then pumped through the assembly under pressure. This flow causes the stationary phase to settle, or pack, at the downstream end of the column with relatively good particle distribution.

In the fourth stage (64), the upper portion of the column assembly (including components 22, 44, and 46) are removed leaving a fully packed chromatography tube (34). In the fifth stage (65), the upstream clamp (22) of stage 3 is attached to the top of the packed chromatography column (34). The piston tube (20) of this upstream clamp (22) is then moved in the downstream direction by rotating the clamp (22) relative to the tube (34) until the interior end thereof (including its porous obstruction (48) (FIG. 2) contacts the settled bed. The column is now ready to run chromatography as described with respect to FIG. 1.

Note that this is one method for packing a chromatography column and that by describing it the applicant does not restrict the application to this one embodiment of a method of packing a chromatography column. Alternatively the packing may be accomplished without extending the column. The consequence of using the method of FIG. 6 without an extension is that whatever volume is occupied by the mobile phase in the slurry mixture will not be available volume for packing the stationary phase. It may also be possible to pack and begin the chromatography process described in FIG. 6 without performing the last two steps (64,65), although in many applications, it may be desirable to maintain the packed stationary phase in place in a way comparable to that described above at the end of stage five (65) in FIG. 6.

It should be understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. A chromatography column, having a longitudinal axis, for use in a liquid chromatography process, said column comprising:
    a chromatography tube;
    a piston tube having an outer diameter smaller than an inner diameter of said chromatography tube;
    said piston tube having at least one porous layer partially obstructing flow through the piston tube;
    at least one chromatography clamp being selectively movable between open and closed positions, and configured to extend substantially 360 degrees about the periphery of said chromatography tube when closed, with no single component of said chromatography clamp extending substantially 360 degrees about said chromatography tube;
    said chromatography clamp having a clamp ledge extending at an oblique angle relative to the transverse direction, the clamp ledge configured to engage the collar ledge to cam the clamp towards the closed position upon application of greater than atmospheric pressure within the column;
    said chromatography clamp configured to releasably maintain said chromatography tube and piston tube in fluid communication with one another.

2. The column of claim 1 wherein at least one end of said chromatography tube is flanged.

3. The column of claim 1 wherein an outer surface of said piston tube is threaded.

4. The column of claim 1 wherein an interior surface of said chromatography clamp is threaded, sized and shaped to threadably engage said piston tube.

5. The column of claim 1 wherein said chromatography clamp is free to rotate relative to a periphery of said chromatography tube.

6. The column of claim 1 wherein said piston tube is held rotationally static relative to said chromatography tube.

7. The column of claim 6 wherein said piston tube is held rotationally static relative to said chromatography tube by an o-ring disposed in a substantially fluid-tight fit between said piston tube and said chromatography tube.

8. The column of claim 1, wherein said angle alpha is approximately 15 degrees or less.

9. The column of claim 8, wherein said angle alpha is within a range of:
    at least about 3 degrees;
    to about 10 degrees.

10. The column of claim 9, wherein said angle alpha is within a range of:
    at least about 4 degrees;
    to about 7 degrees.

11. The column of claim 1, comprising:
    a collar configured to capture said piston tube and to be captured by said chromatography clamp.

12. The column of claim 11, wherein said clamp ledge is configured to engage said collar, to cam the clamp towards the closed position.

13. The column of claim 12, wherein said collar comprises a collar ledge configured to engage said clamp ledge, to cam the clamp towards the closed position.

14. The column of claim 11 comprising a flange disposed at an end of said chromatography tube, and said chromatography clamp is configured to capture said flange and said collar to maintain said chromatography tube and piston tube in axial alignment with one another.

15. The column of claim 14 wherein said collar is held rotationally static relative to said chromatography clamp when said clamp is in the closed position.

16. The column of claim 1, wherein said collar is configured to threadably engage said piston tube.

17. The column of claim 1 wherein said chromatography clamp comprises a hinge configured to permit the clamp to move between said opened and closed positions.

18. The column of claim 1 wherein said chromatography clamp comprises a releasable fastener configured to releasably maintain said chromatography clamp in said closed position.

19. The column of claim 1, comprising porous obstruction substantially permanently disposed at one end of said chromatography tube, said porous obstruction extending across a transverse cross-section of the interior of said tube.

20. The column of claim 1 further comprising:
a filler tube with an opening at both ends;
a column coupling clamp;
said column coupling clamp configured to releasably maintain said chromatography tube and said filler tube in fluid communication with one another.

21. The column of claim 20 wherein at least one end of said filler tube is flanged.

22. The column of claim 20 wherein said column coupling clamp is configured to be bi-directionally openable and closable, to alternately capture and release said chromatography tube by movement substantially in the transverse direction, and to alternately capture and release said column coupling clamp by movement substantially in the axial direction.

23. A chromatography column, having a longitudinal axis, for use in a liquid chromatography process to convey eluent through the column and through an adsorbent disposed within the column, said column comprising:

a chromatography tube;
a piston tube having an outer diameter smaller than an inner diameter of said chromatography tube;
said piston tube having at least one porous layer partially obstructing flow through the piston tube;
a collar configured to capture said piston tube, and having a collar ledge;
at least one chromatography clamp being selectively movable between open and closed positions, and configured to extend substantially 360 degrees about the periphery of said chromatography tube when closed, with no single component of said chromatography clamp extending substantially 360 degrees about said chromatography tube;
said chromatography clamp having a clamp ledge extending at an oblique angle relative to the transverse direction, the clamp ledge configured to engage the collar ledge to cam the clamp towards the closed position upon application of greater than atmospheric pressure within the column;
said chromatography clamp configured to releasably maintain said chromatography tube and said piston tube in fluid communication with one another.

* * * * *